US012582418B2

(12) United States Patent
Trumper

(10) Patent No.: US 12,582,418 B2
(45) Date of Patent: Mar. 24, 2026

(54) KNEE-SURGERY SYSTEM, KNEE-SURGERY ROBOT, AND TECHNIQUES FOR COMPUTER-GUIDED KNEE REPAIR AND/OR KNEE RECONSTRUCTION

(71) Applicant: Rocci V. Trumper, Fort Collins, CO (US)

(72) Inventor: Rocci V. Trumper, Fort Collins, CO (US)

(73) Assignee: 4-Bar Precision Sports Medicine LLC, Fort Collins, CO (US)

( * ) Notice: Subject to any disclaimer, the term of this patent is extended or adjusted under 35 U.S.C. 154(b) by 336 days.

(21) Appl. No.: 18/182,154

(22) Filed: Mar. 10, 2023

(65) Prior Publication Data

US 2023/0285036 A1 Sep. 14, 2023

Related U.S. Application Data

(60) Provisional application No. 63/319,555, filed on Mar. 14, 2022.

(51) Int. Cl.
| | |
|---|---|
| *A61B 34/10* | (2016.01) |
| *A61B 17/16* | (2006.01) |
| *A61B 17/17* | (2006.01) |
| *A61B 34/20* | (2016.01) |
| *A61B 34/30* | (2016.01) |
| *A61B 90/00* | (2016.01) |

(52) U.S. Cl.
CPC ...... *A61B 17/1703* (2013.01); *A61B 17/1675* (2013.01); *A61B 17/1764* (2013.01); *A61B 34/30* (2016.02); *A61B 2034/2055* (2016.02); *A61B 2090/363* (2016.02); *A61B 2090/371* (2016.02); *A61B 2090/3916* (2016.02); *A61B 2090/3937* (2016.02)

(58) Field of Classification Search
CPC ........ A61B 17/1714; A61B 2034/2055; A61B 2034/2065; A61B 17/1703; A61B 2090/395; A61B 2090/3937; A61B 34/20; A61B 2034/2068; A61F 2/0811
See application file for complete search history.

(56) References Cited

U.S. PATENT DOCUMENTS

| | | | |
|---|---|---|---|
| 8,444,652 B2 | 5/2013 | Amis et al. | |
| 2003/0153978 A1 | 8/2003 | Whiteside | |
| 2017/0252173 A1* | 9/2017 | Garino ................. | A61F 2/3859 |
| 2017/0360513 A1* | 12/2017 | Amiot .................... | A61B 34/20 |
| 2022/0202495 A1* | 6/2022 | Pack ...................... | A61B 34/30 |

FOREIGN PATENT DOCUMENTS

WO WO-2020232045 A1 * 11/2020 ............. A61B 34/20

* cited by examiner

*Primary Examiner* — Samuel S Hanna
(74) *Attorney, Agent, or Firm* — Shook, Hardy & Bacon L.L.P.

(57) ABSTRACT

This disclosure describes knee surgery systems, knee surgery robots, components associated with the same, and techniques for computer-guided knee-repair and/or knee-reconstruction.

9 Claims, 6 Drawing Sheets

KNEE-SURGERY SYSTEM, KNEE-SURGERY ROBOT, AND TECHNIQUES FOR COMPUTER-GUIDED KNEE REPAIR AND/OR KNEE RECONSTRUCTION

CROSS-REFERENCE TO RELATED APPLICATIONS

This non-provisional patent application claims priority to U.S. provisional patent app. No. 63/319,555, filed on Mar. 14, 2022, and titled "Knee-Surgery System, Knee-Surgery Robot, and Techniques for Computer-Guided Knee Repair and/or Knee Reconstruction," the contents of which is incorporated herein by reference in the entirety.

TECHNICAL FIELD

The field relates to surgical systems and related technology.

BACKGROUND

The surgical repair of an injured knee and associated tendons, ligaments, and menisci is a complex process that traditionally has relied on extensive surgical experience and practitioner skill. However, because of the many variabilities present when manually repairing, replacing, or augmenting injured tissue in or around the knee, inconsistency in such repairs is common, which frequently results in less than desirable outcomes in patients, e.g., continued pain, lost range of motion, instability, and progressive arthritis and/or arthofibrosis. Thus, improved systems and technologies that allow surgeons to perform such repairs with higher accuracy, consistency, and patient satisfaction, would be beneficial.

SUMMARY

This summary is intended to introduce a selection of concepts in a simplified form that are further described below in the detailed description section of this disclosure. This summary is not intended to identify key or essential features of the claimed subject matter, nor is it intended to be used as an aid in isolation to determine the scope of the claimed subject matter.

In brief, and at a high level, this disclosure describes, among other things, knee surgery systems, knee surgery robots, and techniques for computer-guided knee repair and/or knee reconstruction. The embodiments disclosed herein enable surgeons of different experience levels to perform knee-related repairs and/or reconstructions with a higher degree of precision and consistency and thus enable better outcomes. The systems and components disclosed herein allow for identifying, tracking, and operating based on a unique axis of knee rotation associated with a particular patient and a particular knee repair. In one aspect, to accomplish this, a four-bar linkage is identified for the injured knee. This information is utilized by a computer to determine the axis of rotation defined by the four-bar linkage, and then subsequently, guide the surgeon and robot to precisely control a drilling process, graft placement, and/or tissue repair/augmentation in order to maintain the axis of rotation. The technology supporting this operation which is described herein allows for more accurate, precise, and consistent knee repairs and reconstructions, among other benefits.

In one embodiment, a knee surgery system is provided. The system includes a plurality of trackers, e.g., which may be placed about a patient's knee, e.g., for tracking different parts of the knee geometry. The trackers can use different technologies to indicate or communicate their positions in a three-dimensional space (e.g., a three-dimensional coordinate system in which the knee surgery system operates). For example, in some embodiments, the trackers can use signal triangulation, near-field communications, and/or global positioning system ("GPS") tracking to identify a position of the tracker and thus a position of the associated anatomic structure to which the tracker is attached. The system also includes a marking device that can be used to mark reference points on the knee, either digitally or physically. The system also includes a plurality of cameras that operate to track the locations of the trackers and/or reference points during a knee repair and/or reconstruction process. The system further includes a computing device coupled to the cameras, which can be used to determine and/or triangulate the relative locations of the trackers and/or reference points, to thereby identify and track a four-bar linkage and axis of rotation of a particular knee component, allowing for computer-guided knee repair and/or knee reconstruction. The system further includes a drilling device that is operable for drilling pilot holes and/or tunnels for accurate graft positioning and tensioning as determined by the identified axis of rotation defined by the four-bar linkage. In addition to increased accuracy, precision, and consistency in knee repairs and knee reconstructions, the aforementioned aspects limit the need for traditional mechanical guides, and can increase the efficiency and speed of performing such surgical procedures, among other benefits.

BRIEF DESCRIPTION OF THE DRAWINGS

The embodiments disclosed herein related to knee surgery systems, knee surgery robots, and computer-guided knee repair and/or knee reconstruction are described in detail with reference to the attached figures, which illustrate non-limiting aspects, wherein.

DETAILED DESCRIPTION

This detailed description is provided in order to meet statutory requirements. However, this description is not intended to limit the scope of the invention described herein. Rather, the claimed subject matter may be embodied in different ways, to include different steps, combinations of steps, different elements, and/or different combinations of elements, similar to those described herein, and in conjunction with other present or future technologies and solutions. Moreover, although the terms "step" and "block" may be used herein to identify different elements of methods employed, the terms should not be interpreted as implying any particular order among or between different elements except when the order is explicitly stated.

In general, and at a high level, this disclosure describes knee surgery systems, knee surgery robots, and techniques for computer-guided knee repair and/or knee reconstruction, among other things.

Initially, the geometry of the ligaments of the knee, e.g., the anterior cruciate ligament (hereinafter "ACL") and the posterior cruciate ligament (hereinafter "PCL") help define the central axis of rotation of the knee. This is pertinent to the placement of isometric grafts during ACL surgery, medial collateral ligament (hereinafter "MCL") stabilization, lateral collateral ligament (hereinafter "LCL") reconstruction, and PCL reconstruction, among other things. In addition, the central axis of rotation is directly related to properly tensioning the ACL/PCL grafts and internal brace augmentation during repair and reconstruction procedures.

Figures 1, 2, 3, 4, 5:
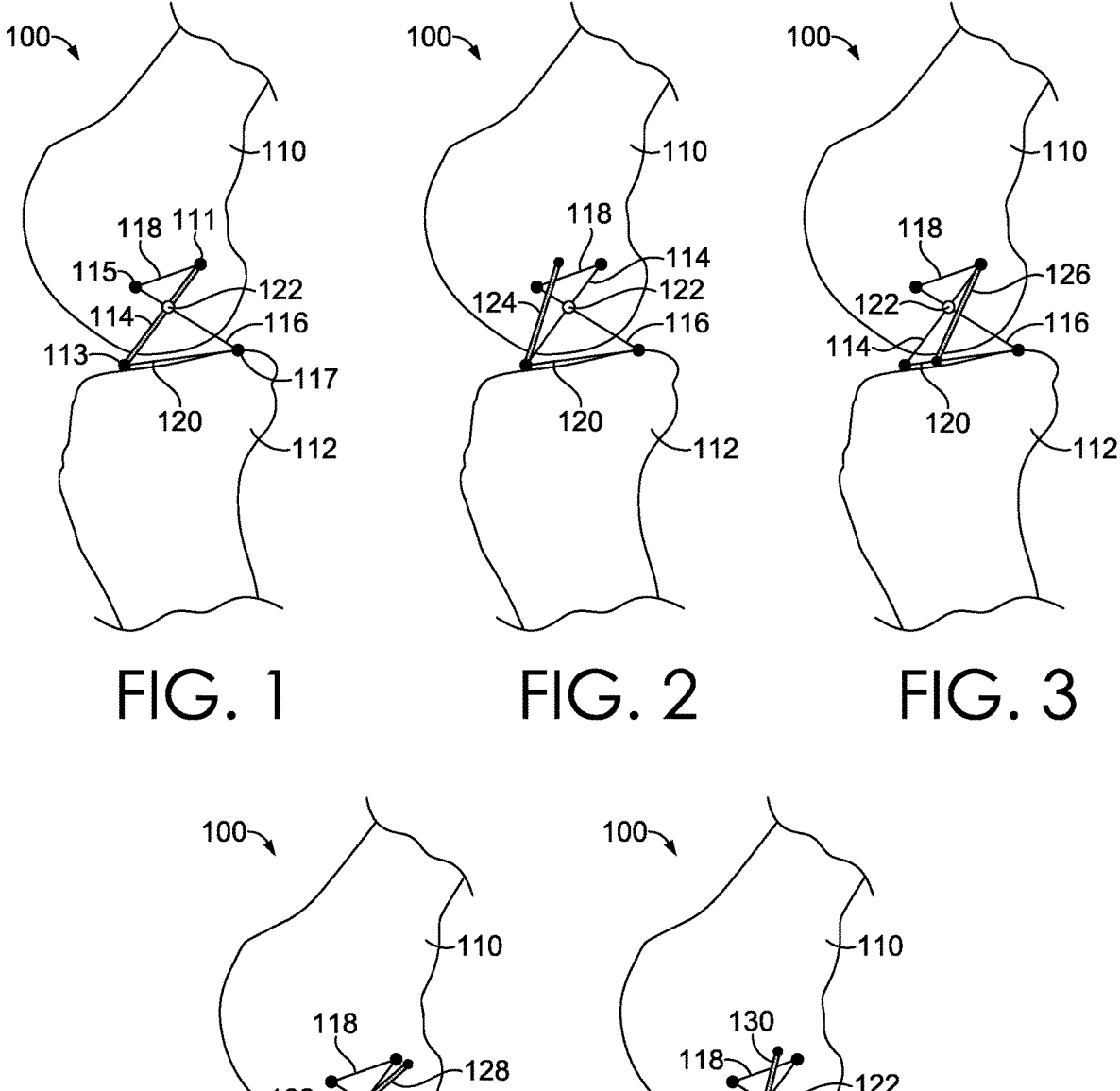
FIG. 1 depicts a side view of a knee joint, a four-bar linkage, and an isometric axis of rotation defined at least in part by the anterior cruciate ligament (ACL) and the posterior cruciate ligament (PCL), in accordance with embodiments of the present disclosure.
FIG. 2 depicts the knee joint of FIG. 1 with an ACL graft positioned anterior to the axis of rotation, in accordance with embodiments of the present disclosure.
FIG. 3 depicts the knee joint of FIG. 1 with an ACL graft positioned posterior to the axis of rotation, in accordance with embodiments of the present disclosure.
FIGS. 4-5 depict the knee joint of FIG. 1 with an ACL graft that is isometric yet malpositioned with respect to origin and insertion, in accordance with embodiments of the present disclosure.

FIG. 1 depicts a side view of a knee joint 100 located between a distal end of a femur 110 and a proximal end of a tibia 112. An anatomic (i.e., not a graft) ACL 114 has an origin 111 located on the femur 110 and an insertion 113 located anteriorly on a tibial plateau of the tibia 112. An anatomic PCL 116 has an origin 115 located on the femur 110 and an insertion 117 located posteriorly on the tibial plateau of the tibia 112. The ACL 114 with its origin 111 and insertion 113 and the PCL 116 with its origin 115 and insertion 117 define a four-bar linkage. The four-bar linkage is the simplest form of movable closed-chain linkage. The four-bar linkage includes a first bar formed by the ACL 114, a second bar formed by the PCL 116, a third bar 118 (also known as a femoral link) formed by a line extending from the origin 111 of the ACL 114 to the origin 115 of the PCL 116, and a fourth bar 120 (also known as a tibial link) formed by a line extending from the insertion 113 of the ACL 114 to the insertion 117 of the PCL 116. The intersection of the ACL 114 and the PCL 116 defines a central or isometric axis of rotation 122.

The unique anatomy of each knee creates challenges to positioning knee reconstruction grafts or internal braces in a position that is as anatomically precise, isometric, and free of impingement as possible. This precision can be critical for improving patient outcomes and minimizing complications, because poorly positioned grafts frequently lead to continued instability, stiffness, and pain. For example, as shown in FIG. 2, during ACL reconstruction, if a graft 124, or augmentation brace, is positioned anterior to the axis of rotation 122, it will be taut in flexion, and loose in extension. In contrast, as shown in FIG. 3, if a graft 126, or augmentation brace, is positioned posterior to the axis of rotation 122, it will be taut in extension, and loose in flexion. FIG. 4 depicts an example, where an ACL graft 128 passes through the axis of rotation 122 (i.e., it is isometric) but is malpositioned in that the origin of the ACL graft 128 is located posterior to the anatomic origin 111 of the anatomic ACL 114, and the insertion of the ACL graft 128 is located anterior to the anatomic insertion 113 of the anatomic ACL 114. FIG. 5 depicts another example where an ACL graft 130 passes through the axis of rotation 122 but is malpositioned in that the origin of the ACL graft 130 is anterior to the anatomic origin 111 of the anatomic ACL 114, and the insertion of the ACL graft 130 is posterior to the anatomic insertion 113 of the anatomic ACL 114. The examples shown in FIGS. 2-4 result in a less than ideal graft position that increases the risk of graft deficiency or failure, continued instability, impingement, stiffness, and/or pain, all of which may lead to poorer patient outcomes. To limit such issues, the four-bar linkage and the axis of rotation 122 can be identified and utilized for more precise tunnel drilling, graft positioning, and tensioning for near-anatomical tissue repair, thereby reducing, limiting, and even substantially eliminating one of the most common reasons for surgical repair complications and failure.

Figure 6:
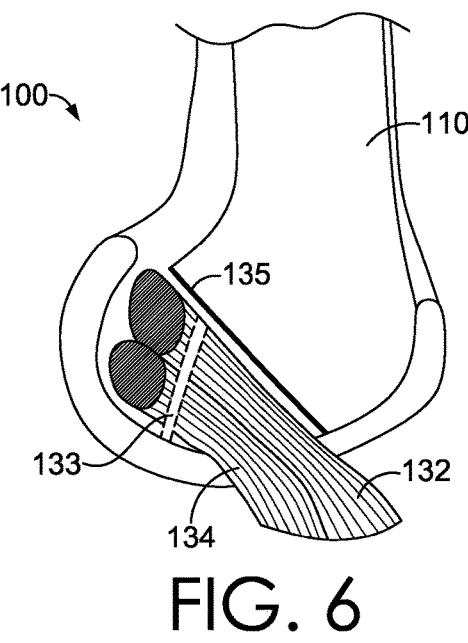
FIG. 6 depicts a portion of the knee joint of FIG. 1 and a two-bundle configuration of a native ACL, in accordance with embodiments of the present disclosure.

FIG. 6 depicts the normal anatomy of the femur 110 of the knee joint 100, including a double bundle ACL construct, which includes an anteromedial bundle 132 and a posterolateral bundle 134. FIG. 6 in addition shows the lateral intercondylar ridge 133, which defines the anterior margin of the ACL 114 origin 111 and the intercondylar roof 135, which is a line drawn along the roof of the intercondylar notch. The intercondylar ridge 133 and the intercondylar roof 135 may be used as reference points during a computer-assisted robotic knee surgery using the embodiments described herein.

Figure 7:
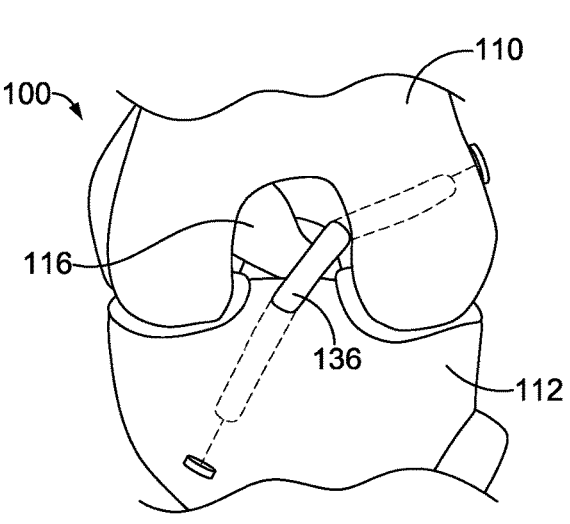
FIG. 7 depicts a front or anterior view of the knee joint of FIG. 1 with a single bundle ACL graft, in accordance with embodiments of the present disclosure.

FIG. 7 depicts a single bundle ACL 136 reconstruction isometrically positioned within the knee joint 100.

Figure 8:
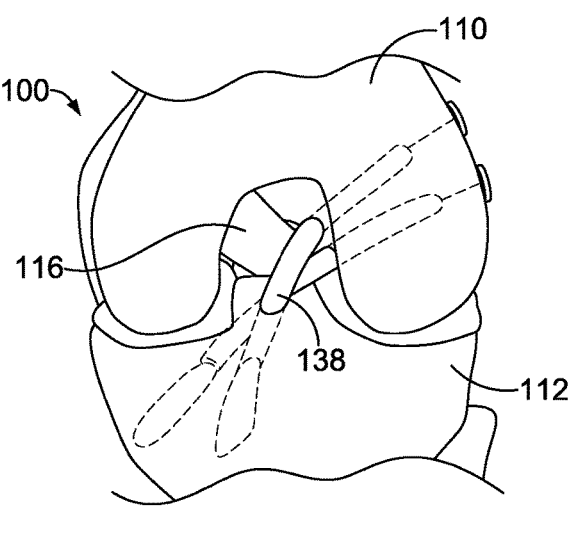
FIG. 8 depicts a front or anterior view of the knee joint of FIG. 1 with a double bundle ACL graft, in accordance with embodiments of the present disclosure.

FIG. 8 depicts a double bundle ACL 138 reconstruction isometrically positioned within the knee joint 100.

Figure 9:
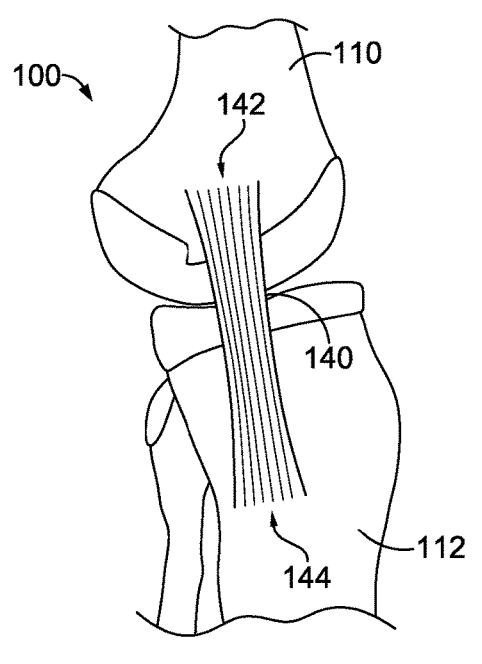
FIG. 9 depicts the knee joint of FIG. 1 and an anatomic medial collateral ligament (MCL), in accordance with embodiments of the present disclosure.

The four-bar linkage and axis of rotation 122 described herein may also be used in determining an appropriate location for a MCL graft. FIG. 9 depicts the knee joint 100 with an anatomic MCL 140 having an origin 142 on the femur 110 and an insertion 144 on the tibia 112. The origin 142 and the insertion 144 of the MCL 140 may also serve as reference points during a robotic knee surgery operation performed using the embodiments described herein.

Figures 10, 11, 12:
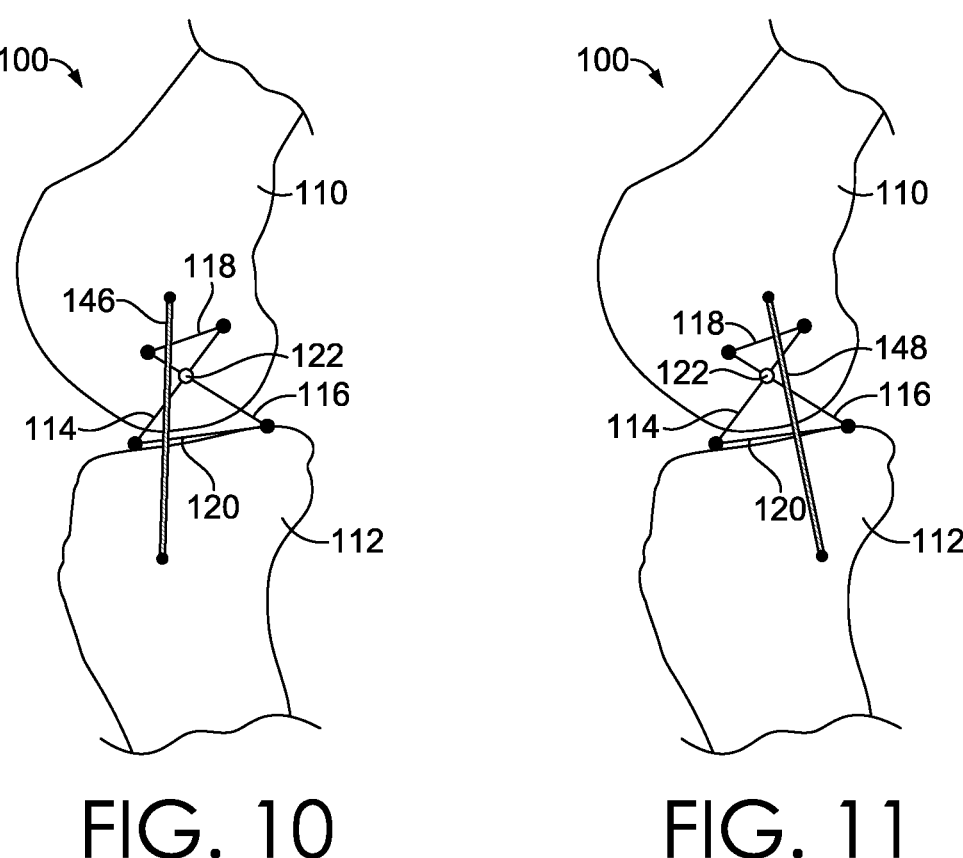
FIG. 10 depicts the knee joint of FIG. 1 with a MCL graft positioned anterior to the axis of rotation, in accordance with embodiments of the present disclosure.
FIG. 11 depicts the knee joint of FIG. 1 with a MCL graft positioned posterior to the axis of rotation, in accordance with embodiments of the present disclosure.
FIG. 12 depicts the knee joint of FIG. 1 with an isometric MCL graft, in accordance with embodiments of the present disclosure.

FIG. 10 depicts the knee joint 100 and a MCL graft 146 that is located anterior to the axis of rotation 122. FIG. 11 depicts the knee joint 100 and a MCL graft 148 that is located posterior to the axis of rotation 122. In these examples, the MCL graft (146 or 148) is out of alignment with the four-bar linkage and the axis of rotation 122. This may result in a less than ideal graft location that does not provide natural movement mechanics in a repaired/reconstructed knee joint, potentially leading to instability or stiffness, which can negatively affect patient outcomes.

FIG. 12 depicts a MCL graft 150 that is positioned isometrically, i.e., through the axis of rotation 122 of the four-bar linkage, which allows the MCL graft 150 to be symmetrically taut in flexion and in extension, thus improving stability and range of motion thereby leading to improved patient outcomes.

The subject matter of this disclosure may be provided as, at least in part, a method, a system, and/or a computer-program product, among other things. Accordingly, certain aspects disclosed herein may take the form of hardware, or may be a combination of software and hardware. A computer-program that includes computer-useable instructions embodied on one or more computer-readable media may also be used. The subject matter hereof may further be implemented as hard-coded into the mechanical design of computing components and/or may be built into a system for performing knee surgery or other related procedures and joint reconstructions (e.g., wrist, elbow, shoulder, ankle, and the like).

Computer-readable media may include volatile media, non-volatile media, removable media, and non-removable media, and may also include media readable by a database, a switch, and/or various other network devices. Network switches, routers, and related components are conventional in nature, as are methods of communicating with the same, and thus, further elaboration is not provided in this disclosure. By way of example, and not limitation, computer-readable media may include computer storage media and/or non-transitory communications media.

Computer storage media, or machine-readable media, may include media implemented in any method or technology for storing information. Examples of stored information include computer-useable instructions, data structures, program modules, and/or other data representations. Computer storage media may include, but is not limited to, RAM, ROM, EEPROM, flash memory or other memory technology, CD-ROM, digital versatile discs (DVD), holographic media or other optical disc storage, magnetic cassettes, magnetic tape, magnetic disk storage, and other storage devices. These memory components may store data momentarily, temporarily, and/or permanently, and are not limited to the examples provided herein.

Figure 13:
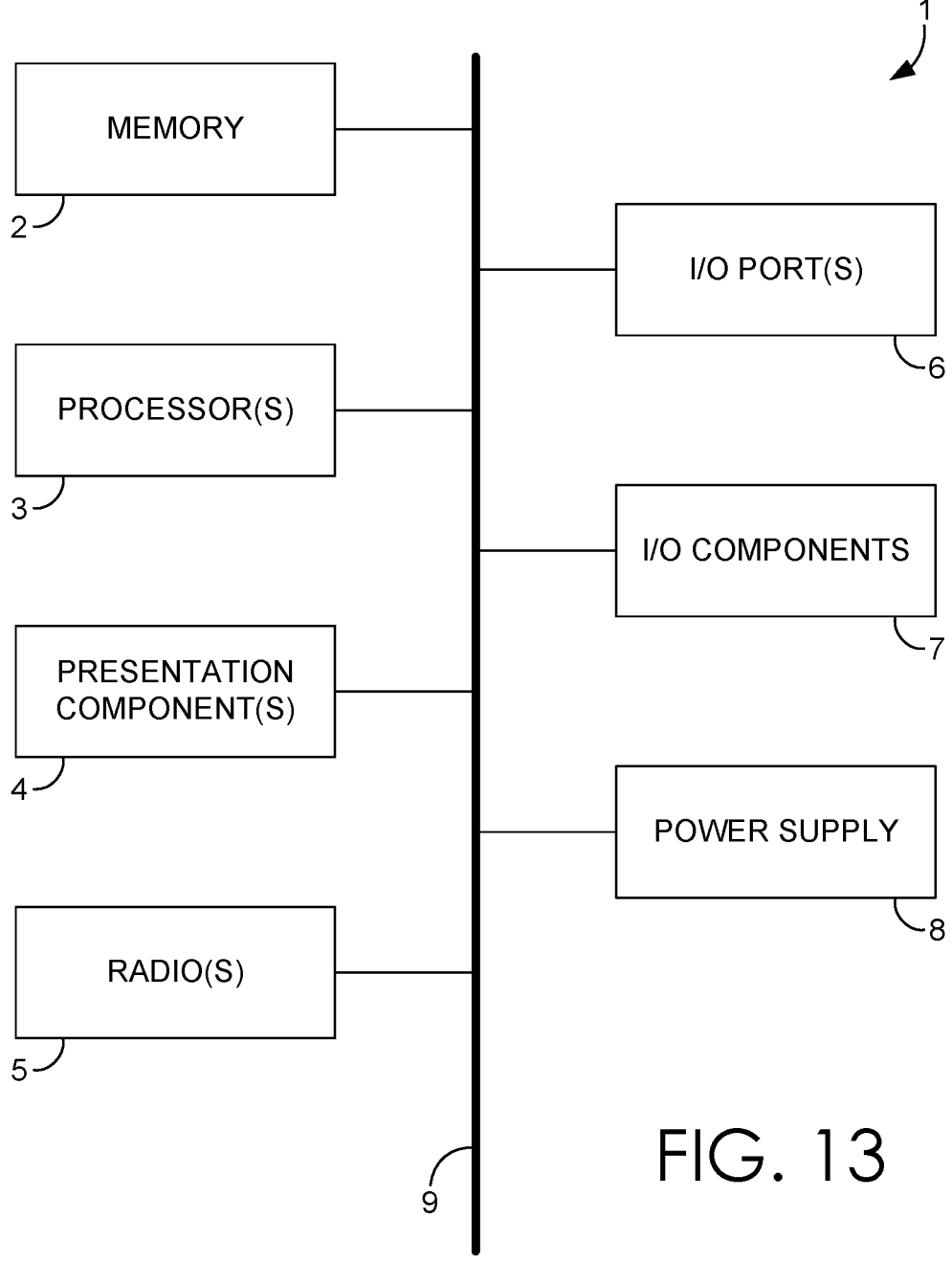
FIG. 13 depicts a computer system suitable for supporting operation of the different embodiments described herein, in accordance with embodiments of the present disclosure.

Looking now at FIG. 13, a block diagram of an example computing device 1 suitable for supporting operation of the systems, devices, and technologies described herein is provided, in accordance with embodiments of the present disclosure. It should be noted that although some components depicted in FIG. 13 are shown in the singular, they may be plural, and the components may be connected in a different, including distributed, configuration. For example, computing device 1 might include multiple processors and/ or multiple memories. As shown in FIG. 13, computing device 1 includes a bus 9 that may directly or indirectly connect different components together, including memory 2, processor(s) 3, presentation component(s) 4 (if applicable), radio(s) 5, input/output (I/O) port(s) 6, input/output (I/O) component(s) 7, and power supply 8.

The memory 2 may take the form of the memory components described herein. Thus, further elaboration will not be provided here, but memory 2 may include any type of tangible medium that is capable of storing information, such as a database. A database may include any collection of records, data, and/or other information. In one embodiment, memory 2 may include a set of computer-executable instructions that, when executed, facilitate various functions or steps associated with the subject matter described herein. These instructions will be referred to as "instructions" or an "application" for short. The processor 3 may actually be multiple processors that may receive instructions and process them accordingly. The presentation component 4 may include a display, a speaker, a screen, a portable digital device, and/or other components that can present information through visual, auditory, and/or other tactile cues (e.g., a display, a screen, a lamp, a light-emitting diode (LED), a graphical user interface (GUI), and/or a lighted keyboard).

The radio 5 may facilitate communication with a network, and may additionally or alternatively facilitate other types of wireless communications, such as Wi-Fi, WiMAX, LTE, Bluetooth, and/or VoIP communications, among other communication protocols. In various aspects, the radio 5 may be configured to support multiple technologies, and/or multiple radios may be configured and utilized to support multiple technologies.

The input/output (I/O) ports 6 may take a variety of forms. Exemplary I/O ports may include a USB jack, a stereo jack, an infrared port, and/or other proprietary or standardized communication ports. The input/output (I/O) components 7 may comprise one or more keyboards, microphones, speakers, touchscreens, and/or any other item useable to directly or indirectly input data into the computing device 1. The power supply 8 may include batteries, generators, fuel cells, and/or any other component that may act as a power source to supply power to computing device 1 and to any other components described herein.

Figure 14:
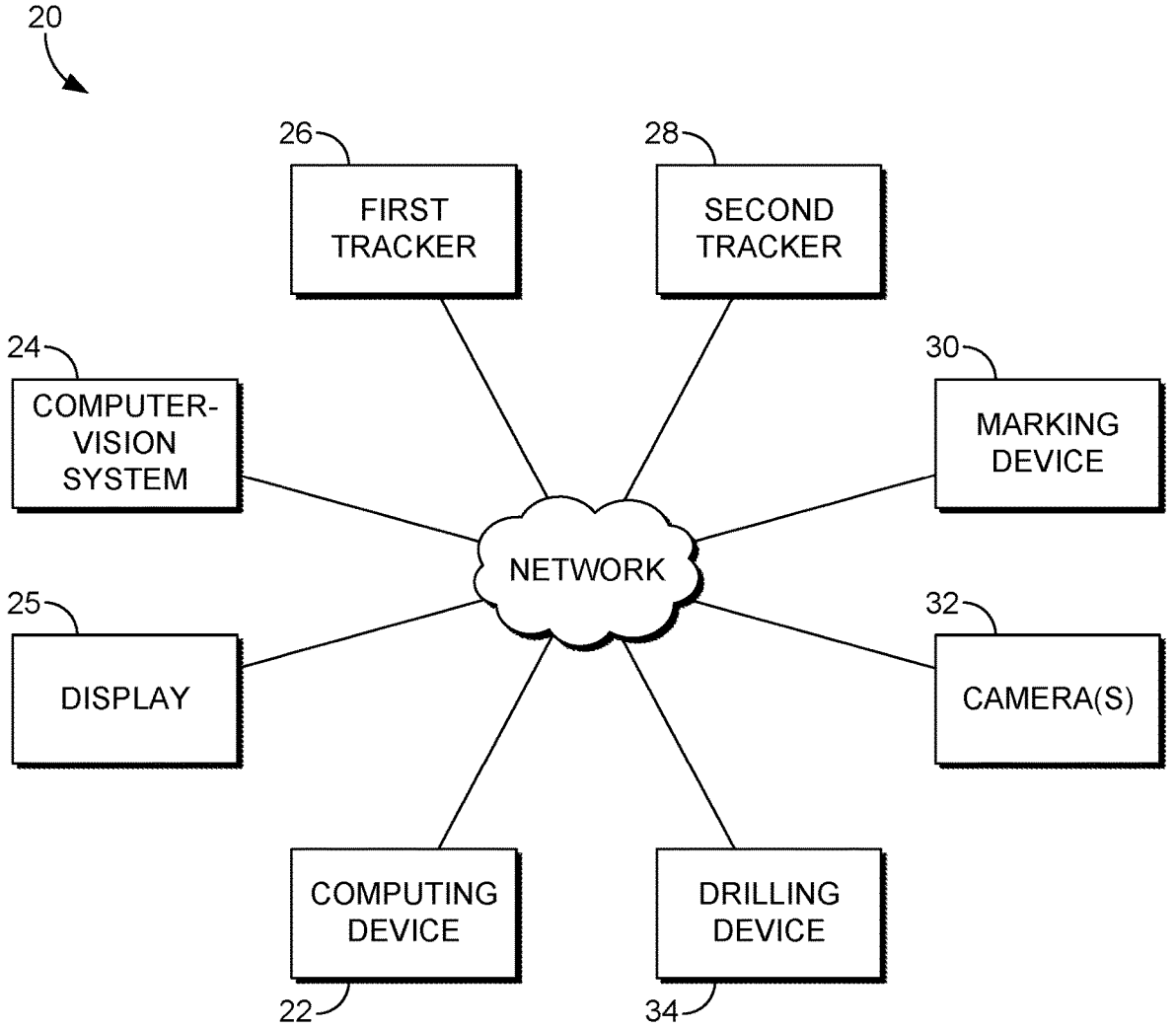
FIG. 14 depicts an example set of components of a knee surgery system, in accordance with embodiments of the present disclosure.

Looking now at FIG. 14, a set of components associated with a surgical system 20 that can be used for knee-related surgical repairs and/or reconstructions is provided, in accordance with embodiments of the present disclosure. The system 20 includes a computing device 22, a display 25, a computer-vision system 24, a first tracker 26, a second tracker 28, a marking device 30, one or more cameras 32, and a drilling device 34. This selection of components shown in FIG. 14 is intended to represent one non-limiting configuration, and numerous other combinations and subcombinations of components are contemplated herein, in different aspects.

The computing device 22 may include one or more processors and one or more memories that support operations carried out using computer-executable instructions.

The trackers 26, 28, and others used during surgical repairs and/or reconstructions, may be sensors that are attachable at different locations on or around a knee joint, such as the knee joint 100, and/or other surrounding anatomical structures. The trackers 26, 28 may be detectable by the cameras 32, the computing device 22, and/or the computer-vision system 24, allowing for determination of the geometric or relative locations of the trackers 26, 28 (e.g., particular geometric coordinates in a three-dimensional geometric coordinate system in which the drilling device 34 also operates). The trackers 26, 28, or other trackers or sensors, may be placed internal or external to the knee joint.

The marking device 30 is used to designate reference points on, within, and/or around a knee joint (or another joint if used in connection with a similar repair and/or reconstruction of such joints). The reference points that are identified may then be tracked using, for example, the camera(s) 32 and/or vision system 24, during knee surgeries to facilitate identification of a four-bar linkage and an axis of rotation such as the axis of rotation 122, and subsequently, to facilitate optimal drilling and graft placement. The reference points that are marked in different procedures may include different attachment points, e.g., that of the ACL, PCL, MCL, or meniscal roots, and may also include the intercondylar roof, and/or intercondylar ridge, among other reference points or areas.

The camera(s) 32 is/are operable to capture images from which the trackers 26, 28 and/or reference points may be identified. For example, the cameras 32 may capture images external to the knee joint (e.g., enabling external detection of trackers connected to or around the knee joint) or internal to the knee joint (e.g., providing internal detection of trackers connected to or around the knee joint). The cameras in the latter instance may be arthroscopic cameras.

The drilling device 34 of the system 20 is used to drill into bone, e.g., on or surrounding a knee joint. The location of the drilling device 34 may also be tracked, e.g., by the cameras (s) 32, computing device 22, and/or computer-vision system 24. The computer-vision system 24 may be connected to the display 25, which allows a location of the reference points, the trackers, and/or the drilling device 34 to be displayed, monitored, and controlled in real-time. This allows for dynamic adjustment of the drilling device 34 in response to the determined location of the four-bar linkage and axis of rotation of the knee joint, e.g., as determined from the trackers.

Figure 15:
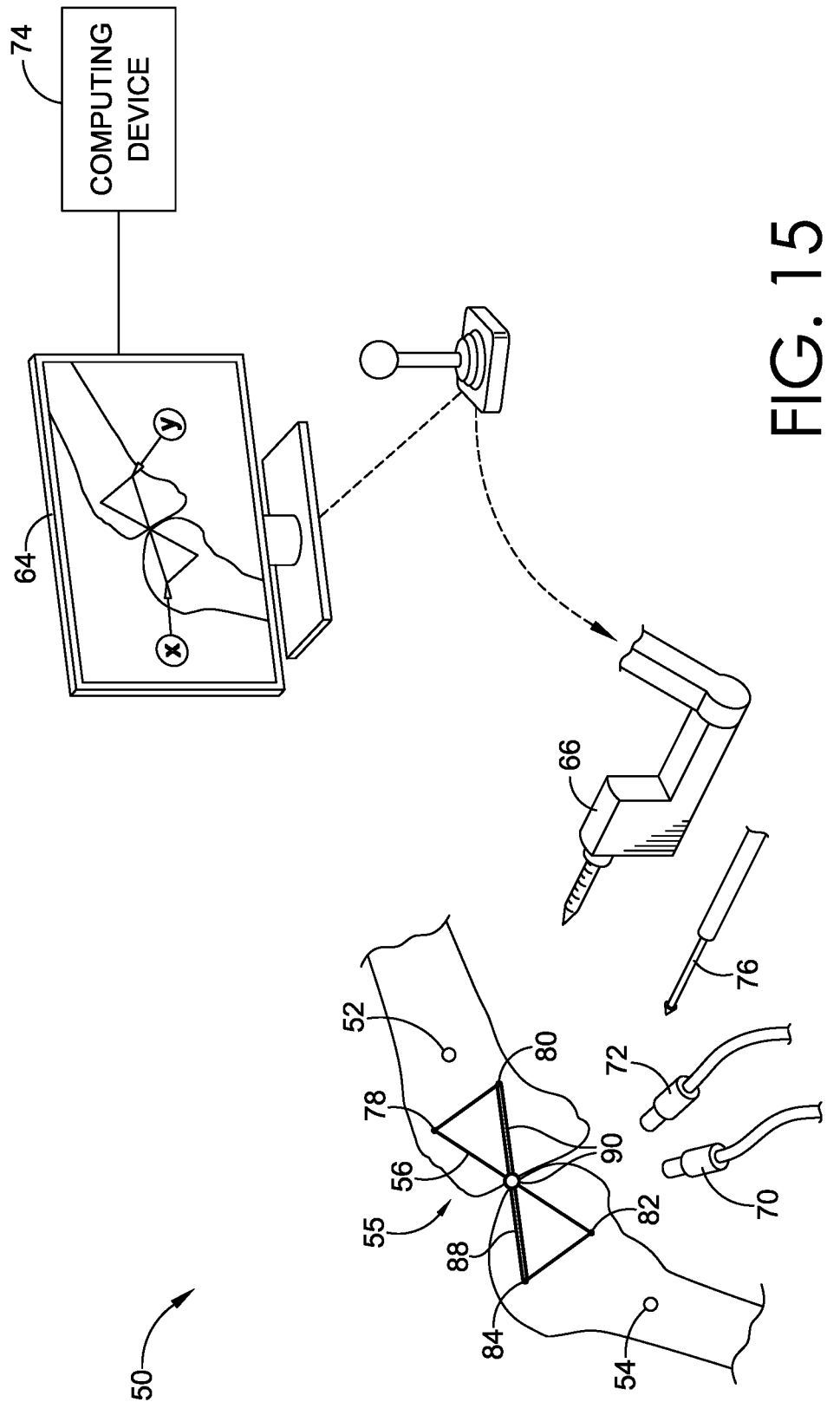
FIG. 15 depicts an example knee surgery system that can be used for knee repair and/or knee reconstruction, in accordance with embodiments of the present disclosure.

Looking now at FIG. 15, an example surgical system 50 used for knee repair and/or knee reconstruction is provided, in accordance with an embodiment of the present disclosure. It should be understood that while knee repairs are discussed primarily herein, the surgical system 50 shown in FIG. 15 and others described herein can also be adapted for similar repairs and/or reconstructions of other joints in connection with a four-bar linkage. For example, the surgical system 50 can be used for repairs and/or reconstructions of wrists, elbows, shoulders, ankles, and the like, in accordance with aspects herein.

The system 50 includes a drilling device 66 used for drilling holes and/or tunnels in or around a knee joint 55, e.g., for isometric graft placement. In addition, the system 50 includes a tracker 52 positioned on a first side of the knee joint 55 (e.g., located on the femur) and a tracker 54 positioned on a second side of the knee joint 55 (e.g., located on the tibia). The trackers 52, 54 are detectable/identifiable by cameras 70, 72 which are located adjacent to the knee joint 55. The cameras 70, 72 are connected to a computing device 74, which is able to determine a relative location and/or position, e.g., a geometric coordinate in a three-dimensional geometric coordinate system, of the trackers 52, 54 during a surgical procedure.

The system 50 also includes a marking device 76, e.g., a marking wand that is operable to mark particular reference points on the knee joint 55, e.g., some of which are identified as elements 78, 80, 82, 84 in FIG. 15. These reference points can be located on, around, or within the knee joint 55. For example, the marked reference points may include different attachment points of ligaments, e.g., ACL, PCL, MCL, and/or may include other anatomical structures, boundaries, and/or locations. These reference points may be used to determine the real-time location of a four-bar linkage 88 and an axis of rotation 90 defined by the four-bar linkage 88, e.g., at each step of a knee-repair and/or knee-reconstruction process. The computing device 74 and cameras 70, 72 are operable to track locations of the trackers 52, 54, the reference points, e.g., 78, 80, 82, 84, and the drilling device 66, allowing the four-bar linkage 88 and axis of rotation 90 to be presented in real-time on the display 64. This allows a surgical operator or computing system to operate, e.g., in automated or semi-automated fashion, or manually, the drilling device 66 to drill holes and/or tunnels in or around the knee joint 55 for graft placement/anchoring, while also allowing the surgical operator to achieve the proper isometry, and align the graft with the axis of rotation. This can also be accomplished with reduced reliance on traditional mechanical guides.

The surgery systems described herein may be used to improve the position and accuracy of sports medicine procedures following knee injury. For example, this can be applied to ligament reconstruction, repair, and/or augmentation. The identification of the four-bar linkage allows surgeons to identify construct geometry, construct position in relation to axis of rotation, proper position for graft/construct tensioning, and construct positioning to eliminate impingement. Using the embodiments described herein, a computer-aided triangulation method can be used for proper positioning of a graft and tensioning, limiting the need for cumbersome mechanical guides or other traditional tools.

To illustrate one example process, in ACL reconstruction, the four-bar linkage can be used to identify the central axis of rotation of the knee, identify the location of graft/construct isometry, identify the best knee position for graft/construct tensioning, identify graft/construct positions for avoiding graft impingement for both the notch and PCL, and can be used for confirming the graft/construct angle in relation to the tibial plateau and intercondylar roof that replicates anatomic ACL positioning. The systems described herein, and a robotic apparatus guided by the same, can then be used for accurate drilling processes in the tibia and the femur for both single and double tunnel ACL reconstruction, again limiting the need for cumbersome mechanical guides and other traditional tools.

To illustrate another process, in PCL reconstruction, the four-bar linkage, being identified by the systems and components described herein, can be used to identify the tibial and femoral tunnel locations, and subsequently, be used for accurately drilling a tibial tunnel and a femoral tunnel, again limiting the need for cumbersome mechanical guides and other traditional tools.

To illustrate another process, in MCL reconstruction, the four-bar linkage, being identified by the systems and components described herein, can be used to accurately identify the anatomical footplate of the MCL attachments on femur and tibia, and identify the position of isometry for graft tensioning.

To illustrate another process, in LCL reconstruction, the four-bar linkage, being identified by the systems and components described herein, can be used to accurately identify a graft position for construct isometry.

To illustrate another process, in meniscal root repairs, the anatomic root position can be identified and marked by the systems and components described herein, and used to accurately drill tunnels from anterior tibia to meniscal footplate, again limiting the need for cumbersome mechanical guides and other traditional tools.

The systems, components, and computer-guided methods of surgical operation described herein may allow for an increase in the accuracy of sports medicine procedures on the knee, particularly for surgeons that only perform a limited number of such procedures.

In further contemplated embodiments, the knee surgery systems, knee surgery robots, and techniques for computer-guided knee repair and/or knee reconstruction described herein may include, utilize, and/or operate in connection with virtual reality ("VR") and/or augmented reality ("AR") systems, components, and technologies. For example, when performing a computer-guided knee-repair and/or knee-reconstruction, a knee surgery system, e.g., such as the surgical system 50 shown in FIG. 15, may use AR or VR components to allow a surgeon to operate using real-time visual feedback. For example, during an operation, a surgeon may be able to see through AR and/or VR components different visual indicators, e.g., trackers, anatomic locations, four-bar linkages, axes of rotation, and/or drilling locations, among others. This visual feedback may be provided in one instance with a AR or VR headset/eyewear system.

Embodiment 1. A system for guiding surgical knee-repair and/or knee-reconstruction, the system comprising: a first tracker attachable to a first location selected around a knee joint; a second tracker attachable to a second location selected around the knee joint, wherein the first location and the second location are movable in relation to each other; a marking device operable to mark a plurality of reference points on the knee joint; a plurality of cameras operable to capture a plurality of images of the first tracker, the second tracker, and the plurality of reference points; a computing device configured to: detect relative positions of the first tracker, the second tracker, and/or the plurality of reference points from the plurality of images, identify a four-bar linkage of the knee joint based on the relative positions of the first tracker, the second tracker, and/or the plurality of reference points, and identify an axis of rotation of the knee joint defined by the four-bar linkage; and a drilling device operable to drill one or more holes and/or tunnels around the knee joint, wherein the drilling device is guidable for drilling the one or more holes and/or tunnels around the knee joint based on the axis of rotation and the relative positions of the first tracker, the second tracker, and/or the plurality of reference points.

Embodiment 2. The system of embodiment 1, wherein the plurality of reference points include one or more of: attachment points of one or more knee ligaments; a location of an intercondylar roof; a location of one or more meniscal roots; and a location of an intercondylar lateral ridge.

Embodiment 3. The system of embodiment 1 or 2, wherein the drilling device is robotically guided.

Embodiment 4. The system of any of embodiments 1-3, wherein the marking device is a manually operable marking wand.

Embodiment 5. The system of any of embodiments 1-4, wherein the first tracker and the second tracker each comprise a sensor detectable by the plurality of cameras and the computing device.

Embodiment 6. The system of any of embodiments 1-5, wherein the plurality of cameras comprise a plurality of arthroscopic cameras.

Embodiment 7. The system of any of embodiments 1-6, wherein the computing device comprises a computer-vision system with a display that depicts one or more of the four-bar linkage and the axis of rotation of the knee joint during drilling of the holes and/or tunnels, thereby identifying locations on the knee joint for isometric placement of a graft.

Embodiment 8. A method for surgical knee-repair and/or knee-reconstruction, the method comprising: attaching a first tracker to a first location selected around a knee joint; attaching a second tracker to a second location selected around the knee joint, wherein the first location and the second location are movable with respect to each other; marking a plurality of reference points on the knee joint using a marking device; operating one or more cameras to capture a plurality of images of the first tracker, the second tracker, and the plurality of reference points; operating a computing device to: detect relative positions of the first tracker, the second tracker, and/or the plurality of reference points from the plurality of images, identify a four-bar linkage of the knee joint based on the relative positions of the first tracker, the second tracker, and/or the plurality of reference points, and identify an axis of rotation of the knee joint defined by the four-bar linkage; and guiding a drilling device to drill one or more holes and/or tunnels around the knee joint based on one or more of the identified axis of rotation and the relative positions of the first tracker, the second tracker, and/or the plurality of reference points.

Embodiment 9. The method of embodiment 8, wherein the plurality of reference points include one or more of: attachment points of one or more knee ligaments; a location of an intercondylar roof; a location of one or more meniscal roots; and a location of an intercondylar lateral ridge.

Embodiment 10. The method of embodiment 8 or 9, wherein the drilling device is robotically guided.

Embodiment 11. The method of any of embodiments 8-10, wherein the marking device is a manually operable marking wand.

Embodiment 12. The method of any of embodiments 8-11, wherein the first tracker and the second tracker each comprise a sensor detectable by the one or more cameras and the computing device.

Embodiment 13. The method of any of embodiments 8-12, wherein the one or more cameras comprise a plurality of arthroscopic cameras.

Embodiment 14. The method of any of embodiments 8-13, wherein the computing device comprises part of a computer-vision system with a display that depicts one or more of the four-bar linkage and the axis of rotation of the knee joint during drilling of the one or more holes and/or tunnels, thereby identifying locations on the knee joint for isometric placement of a graft.

Embodiment 15. The method of any of embodiments 8-14, further comprising: displaying the axis of rotation and the plurality of reference points with an augmented reality system; or displaying the axis of rotation and the plurality of reference points with a virtual reality system.

Embodiment 16. One or more computer storage media storing computer-useable instructions that, when used by one or more computing devices, cause the one or more computing devices to perform operations comprising: detecting relative positions of a first tracker positioned at a first location around a knee joint, a second tracker positioned at a second location around the knee joint, and a plurality of reference points marked on the knee joint; identify a four-bar linkage of the knee joint based on the relative positions of the first tracker, the second tracker, and the plurality of reference points; identify an axis of rotation of the knee joint defined by the four-bar linkage; and guide a drilling device to drill one or more holes or channel around the knee joint based on the one or more of the identified axis of rotation and the relative positions of the one or more of the first tracker, the second tracker, and the plurality of reference points.

Embodiment 17. The one or more computer storage media of embodiment 16, wherein the first location of the first tracker and the second location of the second tracker are movable in relation to each other.

Embodiment 18. The one or more computer storage media of embodiment 16 or 17, wherein a plurality of cameras capture a plurality of images of the first tracker, the second tracker, and the plurality of reference points, and wherein the plurality of images are used to detect the relative positions of the first tracker, the second tracker, and the plurality of reference points.

Embodiment 19. The one or more computer storage media of any of embodiments 16-18, wherein the relative positions of the first tracker, the second tracker, and the plurality of reference points represent geometric coordinates in a three-dimensional geometric coordinate system.

Embodiment 20. The one or more computer storage media of any of embodiments 16-19, wherein the drilling device operates in the three-dimensional geometric coordinate system.

Embodiment 21. The one or more computer storage media of any of embodiments 16-20, wherein the plurality of reference points include one or more of: attachment points of one or more knee ligaments; a location of an intercondylar roof; a location of one or more meniscal roots; and a location of an intercondylar lateral ridge.

Embodiment 22. The preceding embodiments 1-21 in any combination or sub-combination.

In some embodiments, this disclosure may include the language, for example, "at least one of [element A] and [element B]." This language may refer to one or more of the elements. For example, "at least one of A and B" may refer to "A," "B," or "A and B." In other words, "at least one of A and B" may refer to "at least one of A and at least one of B," or "at least either of A or B." In some embodiments, this disclosure may include the language, for example, "[element A], [element B], and/or [element C]." This language may refer to either of the elements or any combination thereof. In other words, "A, B, and/or C" may refer to "A," "B," "C," "A and B," "A and C," "B and C," or "A, B, and C." In addition, this disclosure may use the term "and/or" which may refer to any one or combination of the associated elements.

The subject matter of this disclosure has been described in relation to particular embodiments, which are intended in all respects to be illustrative rather than restrictive. In this sense, alternative embodiments will become apparent to those of ordinary skill in the art to which the present subject matter pertains without departing from the scope hereof. In addition, different combinations and sub-combinations of elements disclosed, as well as use and inclusion of elements not shown, are possible and contemplated as well.

What is claimed is:

1. A method for surgical knee-repair and/or knee-reconstruction, the method comprising:

attaching a first tracker to a first location selected around a knee joint;

attaching a second tracker to a second location selected around the knee joint, wherein the first location and the second location are movable with respect to each other;

marking a plurality of reference points on the knee joint using a marking device;

operating one or more cameras to capture a plurality of images of the first tracker, the second tracker, and the plurality of reference points;

operating a computing device to:

detect relative positions of the first tracker, the second tracker, and/or the plurality of reference points from the plurality of images, identify a four-bar linkage of the knee joint based on the relative positions of the first tracker, the second tracker, and/or the plurality of reference points, and identify an axis of rotation of the knee joint defined by the four-bar linkage, wherein identifying the axis of rotation comprises identifying a point of isometry that is defined by intersecting segments of the four-bar linkage; and guiding a drilling device to drill one or more holes and/or tunnels around the knee joint based on one or more of the identified axis of rotation and the relative positions of the first tracker, the second tracker, and/or the plurality of reference points.

2. The method of claim 1, wherein the plurality of reference points include one or more of:

attachment points of one or more knee ligaments;

a location of an intercondylar roof;

a location of one or more meniscal roots; and a location of an intercondylar lateral ridge.

3. The method of claim 1, wherein the drilling device is robotically guided.

4. The method of claim 1, wherein the marking device is a manually operable marking wand.

5. The method of claim 1, wherein the first tracker and the second tracker each comprise a sensor detectable by the one or more cameras and the computing device.

6. The method of claim 1, wherein the one or more cameras comprise a plurality of arthroscopic cameras.

7. The method of claim 1, wherein the computing device comprises part of a computer-vision system with a display that depicts one or more of the four-bar linkage and the axis of rotation of the knee joint during drilling of the one or more holes and/or tunnels, thereby identifying locations on the knee joint for isometric placement of a graft.

8. The method of claim 1, further comprising displaying the axis of rotation and the plurality of reference points using an augmented reality system during the guiding of the drilling device.

9. The method of claim 1, further comprising displaying the axis of rotation and the plurality of reference points using a virtual reality system during the guiding of the drilling device.

* * * * *